(12) United States Patent
Yip et al.

(10) Patent No.: US 11,931,282 B2
(45) Date of Patent: Mar. 19, 2024

(54) BRACEWEAR FOR SPINAL CORRECTION AND SYSTEM FOR POSTURE TRAINING

(71) Applicant: THE HONG KONG POLYTECHNIC UNIVERSITY, Hong Kong (CN)

(72) Inventors: Yiu-Wan Joanne Yip, Hong Kong (CN); Yin Ling Sit, Hong Kong (CN); Ting Hin Mak, Hong Kong (CN); Kit Lun Yick, Hong Kong (CN); Tsz Hei Cheung, Hong Kong (CN); Sui Pui Ng, Hong Kong (CN); Kenny Yat Hong Kwan, Hong Kong (CN); Mei Chun Cheung, Hong Kong (CN); Ming Fai Chan, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 815 days.

(21) Appl. No.: 17/071,070

(22) Filed: Oct. 15, 2020

(65) Prior Publication Data

US 2022/0117769 A1     Apr. 21, 2022

(51) Int. Cl.
*A61F 5/02*      (2006.01)
*A61B 5/00*      (2006.01)

(52) U.S. Cl.
CPC ............ *A61F 5/026* (2013.01); *A61B 5/4561* (2013.01); *A61B 5/486* (2013.01); *A61B 5/6805* (2013.01); *A61B 5/7405* (2013.01); *A61B 5/742* (2013.01); *A61B 5/7455* (2013.01); *A61F 5/024* (2013.01); *A61B 2562/0219* (2013.01)

(58) Field of Classification Search
CPC .... A61F 5/024; A61F 5/026; A61F 5/02–028; A61B 5/6805; A61B 5/1116; A61B 5/4561; A61B 5/486; A61B 5/7405; A61B 5/742; A61B 5/7455; A61B 2562/0219; A61B 5/6804; Y10S 2/913; A41D 1/04; A41D 1/00–22
USPC .......................................................... 602/19
See application file for complete search history.

(56) References Cited

U.S. PATENT DOCUMENTS

| | | |
|---|---|---|
| 5,782,782 A | 7/1998 | Miller |
| 6,676,617 B1 | 1/2004 | Miller |
| 7,766,850 B2 | 8/2010 | Simanovsky |

(Continued)

FOREIGN PATENT DOCUMENTS

| | | |
|---|---|---|
| GB | 2467974 A | 8/2010 |
| TW | 201106933 A1 | 3/2011 |

OTHER PUBLICATIONS

Sit et al.; A New Concept for Adult Degenerative Scoliosis: Posture Training Bracewear; Proceedings of ISERD International Conference, Zurich, Switzerland, Feb. 16-17, 2020; pp. 5-7.

(Continued)

*Primary Examiner* — Rachael E Bredefeld
*Assistant Examiner* — Seth R. Brown
(74) *Attorney, Agent, or Firm* — Spruson & Ferguson (Hong Kong) Limited (57) ABSTRACT

The present disclosure provides a bracewear for spinal correction and a system for posture training. The system for posture training involves both active and passive corrective forces by using the bracewear and a biofeedback system to address the spinal correction, which can eliminate the adversity of conventional hard braces and reduce the psychological and physiological barriers to treatment.

16 Claims, 12 Drawing Sheets

(Front)          (Back)

(56) References Cited

U.S. PATENT DOCUMENTS

| | | |
|---|---|---|
| 9,155,651 B2 | 10/2015 | Ochoa |
| 2009/0054818 A1 | 2/2009 | Kaufman et al. |
| 2012/0059297 A1 | 3/2012 | Newkirk |
| 2012/0316483 A1* | 12/2012 | Waeger .................. A61F 5/026 602/19 |
| 2013/0184625 A1 | 7/2013 | Ingimundarson et al. |
| 2015/0094633 A1* | 4/2015 | Garcia .................. A61F 5/026 602/19 |
| 2015/0148727 A1* | 5/2015 | Collier .................. A61F 5/026 602/19 |
| 2017/0079828 A1 | 3/2017 | Pedtke et al. |
| 2017/0156911 A1 | 6/2017 | Ingimundarson et al. |
| 2019/0029866 A1* | 1/2019 | Stier ...................... A61F 5/026 |
| 2020/0352476 A1* | 11/2020 | Ladd ...................... A61B 5/486 |
| 2021/0007874 A1* | 1/2021 | Galiana Bujanda .... A61F 5/028 |

OTHER PUBLICATIONS

International Search Report and Written Opinion of PCT application No. PCT/CN2021/090853 issued from the International Search Authority dated Aug. 2, 2021.

* cited by examiner

BRACEWEAR FOR SPINAL CORRECTION AND SYSTEM FOR POSTURE TRAINING

PRIOR DISCLOSURE BY THE INVENTOR OR A JOINT INVENTOR

Part of the present invention was disclosed in a paper published in the Proceedings of ISERD International Conference, Zurich, Switzerland, with a title: A New Concept for Adult Degenerative Scoliosis: Posture Training Bracewear on 16 and 17 Feb. 2020. The paper is a grace period inventor-originated disclosure disclosed within one year before the effective filing date of this application.

TECHNICAL FIELD

The present disclosure relates to a bracewear for spinal correction and a system for posture training.

BACKGROUND

The average life expectancy of humans has greatly increased since the last decade due to medical advancements that improve health and quality of life. However, the rapid increase in the ageing population also raises the possibility of increase in cases of non-communicable diseases, such as musculoskeletal disorders. Many researches have indicated that many of the elderly experience musculoskeletal pain and/or suffer from lower back pain. Lower back pain is a common medical condition in older adults which is mainly caused by injury, disease or degeneration of the spine.

One such degenerative condition is called adult degenerative scoliosis (ADS), which is found in the ageing population who have a Cobb's angle that is 10 degrees or larger in the coronal plane of the spine. There have been growing concerns about the effects of ADS on health due to its increasing prevalence. Aside from an asymmetric trunk and sagittal imbalance, ADS patients usually experience lower back pain and/or have symptomatic lumbar stenosis. The reason for ADS is because the general health and bone quality of older adults deteriorate more in comparison to younger adults. They also face more risks during surgery to correct ADS and thus bracing, which is one of the most common conservative treatments, is usually recommended as a treatment option. The aim of bracing is to stabilize the spine and relieve chronic back pain. ADS patients can choose different types of spinal orthoses, e.g., rigid or flexible braces. However, the effectiveness of the conventional braces is under debate. Moreover, over-reliance on bracing will reduce muscle activity especially in ADS patients. Therefore, a supervised exercise regime that focuses on strengthening the core muscles and postural training is also typically recommended for treatment.

A need therefore exists for an improved bracewear and system for posture training that eliminates or at least diminishes the disadvantages and problems described above.

SUMMARY

Provided herein is a bracewear for spinal correction for a wearer comprising: a vest wearable by the wearer; a waistband for surrounding an abdomen of the wearer; one or more back struts arranged to be attached to a back of the vest for supporting a spine of the wearer; a rigid connector arranged to overlie the one or more back struts for applying a force to the one or more back struts; and a strap assembly comprising: a first shoulder strap for surrounding a left shoulder of the wearer and a left side of a pelvis of the wearer, a first end of the first shoulder strap being attachable to the waistband; and a second shoulder strap for surrounding a right shoulder of the wearer and a right side of the pelvis, a first end of the second shoulder strap being attachable to the waistband; wherein the first shoulder strap, the second shoulder strap and the rigid connector are configured to connect the first shoulder strap and the second shoulder strap to the rigid connector such that when the first shoulder strap and the second shoulder strap are under tension, the rigid connector applies the force to the one or more back struts so as to correct alignment of the spine.

In certain embodiments, the rigid connector comprises: a first slot for connecting to a second end of the first shoulder strap and a second end of the second shoulder strap; a second slot for allowing the first shoulder strap to pass through; and a third slot for allowing the second shoulder strap to pass through.

In certain embodiments, the rigid connector comprises: a first slot for connecting to a second end of the first shoulder strap; a second slot for connecting to a second end of the second shoulder strap; a third slot for allowing the first shoulder strap to pass through; and a fourth slot for allowing the second shoulder strap to pass through.

In certain embodiments, the first shoulder strap comprises a first non-elastic portion and a first elastic portion, the first non-elastic potion being used for surrounding the left shoulder, the first elastic portion being used for connecting to the rigid connector and surrounding the left side of the pelvis; and the second shoulder strap comprises a second non-elastic portion and a second elastic portion, the second non-elastic potion being used for surrounding the right shoulder, the second elastic portion being used for connecting to the rigid connector and surrounding the right side of the pelvis.

In certain embodiments, each of the first non-elastic portion and the second non-elastic portion comprises a laminated neoprene fabric; and each of the first elastic portion and the second elastic portion comprises a knitted fabric.

In certain embodiments, the strap assembly further comprises: a first length adjuster for adjusting a length of the first shoulder strap; and a second length adjuster for adjusting a length of the second shoulder strap.

In certain embodiments, each of the one or more back struts has a curvature fitting the spine.

In certain embodiments, the vest comprises one or more strut casings attached to the back of the vest for holding the one or more back struts respectively.

In certain embodiments, the vest comprises a connector fixer attached to the back of the vest for fixing the rigid connector to overlie the one or more back struts.

In certain embodiments, the connector fixer comprises a strap for passing through one or more slots of the rigid connector.

In certain embodiments, the vest has a separable collar and comprises a front hole located below the separable collar.

In certain embodiments, the bracewear further comprises: one or more posture monitoring sensors attachable to the back of the vest for monitoring a posture of the wearer; an alerting device for alerting the wearer when the wearer is in poor posture; and a controller configured to: determine the posture from a signal from the one or more posture sensors; and control the alerting device for alerting the wearer when the wearer is in poor posture.

Provided herein is a system for posture training for a wearer comprising: the bracewear described above; and a biofeedback system comprising: one or more posture monitoring sensors attachable to the back of the vest for monitoring a posture of the wearer; an alerting device for alerting the wearer when the wearer is in bad posture; and a controller configured to: determine the posture from a signal of the one or more posture sensors; and control the biofeedback device to alert the wearer when the wearer is in bad posture.

In certain embodiments, each of the one or more posture monitoring sensors is an inertial measurement unit for measuring orientation of a spine of the wearer.

In certain embodiments, the alerting device is a vibrator or a buzzer.

In certain embodiments, the controller is further configured to determine a posture rating of the wearer from the signal of the one or more posture sensors.

In certain embodiments, the biofeedback system further comprises a display for displaying the posture rating.

In certain embodiments, the one or more posture monitoring sensors are attached to the back of the vest; and the alerting device is attached to a collar of the vest.

Provided herein is a system for posture training for a wearer comprising: a vest wearable by the wearer; and a biofeedback system comprising: one or more posture monitoring sensors attachable to a back of the vest for monitoring a posture of the wearer; an alerting device for alerting the wearer when the wearer is in bad posture; and a controller configured to: determine the posture from a signal of the one or more posture sensors; and control the biofeedback device to alert the wearer when the wearer is in bad posture.

Provided herein is a biofeedback system comprising: one or more posture monitoring sensors for monitoring a posture of a user; an alerting device for alerting the user when the user is in bad posture; and a controller configured to: determine the posture from a signal of the one or more posture monitoring sensors; and control the alerting device to alert the wearer when the wearer is in bad posture.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

The present disclosure provides a bracewear for spinal correction and a system for posture training. The system for posture training involves both active and passive corrective forces by using the bracewear and a biofeedback system to address the spinal correction, which can eliminate the adversity of conventional hard braces and reduce the psychological and physiological barriers to treatment.

The present disclosure provides a bracewear for spinal correction for a wearer comprising: a vest wearable by the wearer: a waistband for surrounding an abdomen of the wearer; one or more back struts arranged to be attached to a back of the vest for supporting a spine of the wearer; a rigid connector arranged to overlie the one or more back struts for applying a force to the one or more back struts; and a strap assembly comprising: a first shoulder strap for surrounding a left shoulder of the wearer and a left side of a pelvis of the wearer, a first end of the first shoulder strap being attachable to the waistband; and a second shoulder strap for surrounding a right shoulder of the wearer and a right side of the pelvis, a first end of the second shoulder strap being attachable to the waistband; wherein the first shoulder strap, the second shoulder strap and the rigid connector are configured to connect the first shoulder strap and the second shoulder strap to the rigid connector such that when the first shoulder strap and the second shoulder strap are under tension, the rigid connector applies the force to the one or more back struts so as to correct alignment of the spine.

In certain embodiments, the rigid connector comprises: a first slot for connecting to a second end of the first shoulder strap and a second end of the second shoulder strap; a second slot for allowing the first shoulder strap to pass through; and a third slot for allowing the second shoulder strap to pass through.

In certain embodiments, the rigid connector comprises: a first slot for connecting to a second end of the first shoulder strap; a second slot for connecting to a second end of the second shoulder strap; a third slot for allowing the first shoulder strap to pass through; and a fourth slot for allowing the second shoulder strap to pass through.

In certain embodiments, the first shoulder strap comprises a first non-elastic portion and a first elastic portion, the first non-elastic potion being used for surrounding the left shoulder, the first elastic portion being used for connecting to the rigid connector and surrounding the left side of the pelvis; and the second shoulder strap comprises a second non-elastic portion and a second elastic portion, the second non-elastic potion being used for surrounding the right shoulder, the second elastic portion being used for connecting to the rigid connector and surrounding the right side of the pelvis.

In certain embodiments, each of the first non-elastic portion and the second non-elastic portion comprises a laminated neoprene fabric; and each of the first elastic portion and the second elastic portion comprises a knitted fabric.

In certain embodiments, the strap assembly further comprises: a first length adjuster for adjusting a length of the first shoulder strap; and a second length adjuster for adjusting a length of the second shoulder strap.

In certain embodiments, each of the one or more back struts has a curvature fitting the spine.

In certain embodiments, the vest comprises one or more strut casings attached to the back of the vest for holding the one or more back struts respectively.

In certain embodiments, the vest comprises a connector fixer attached to the back of the vest for fixing the rigid connector to overlie the one or more back struts.

In certain embodiments, the connector fixer comprises a strap for passing through one or more slots of the rigid connector.

In certain embodiments, the vest has a separable collar and comprises a front hole located below the separable collar.

In certain embodiments, the bracewear further comprises: one or more posture monitoring sensors attachable to the back of the vest for monitoring a posture of the wearer; an alerting device for alerting the wearer when the wearer is in poor posture; and a controller configured to: determine the posture from a signal from the one or more posture sensors; and control the alerting device for alerting the wearer when the wearer is in poor posture.

In certain embodiments, the rigid connector comprises an alloy, aluminum, acrylic or polyamide (e.g., nylon).

In certain embodiments, the non-elastic portion of the shoulder strap comprises a cotton woven fabric, a nylon woven fabric, a polyester woven fabric or a nylon/polyester strap.

In certain embodiments, the elastic portion of the shoulder strap comprises a cotton spandex knitted fabric, a nylon spandex knitted fabric or a polyester spandex knitted fabric.

In certain embodiments, the back strut comprises a shape memory alloy, an alloy, a resin, polylactide (PLA) or acrylonitrile butadiene styrene (ABS).

The present disclosure provides a system for posture training for a wearer comprising: the bracewear described above; and a biofeedback system comprising: one or more posture monitoring sensors attachable to the back of the vest for monitoring a posture of the wearer; an alerting device for alerting the wearer when the wearer is in bad posture; and a controller configured to: determine the posture from a signal of the one or more posture sensors; and control the biofeedback device to alert the wearer when the wearer is in bad posture.

In certain embodiments, each of the one or more posture monitoring sensors is an inertial measurement unit for measuring orientation of a spine of the wearer.

In certain embodiments, the alerting device is a vibrator or a buzzer.

In certain embodiments, the controller is further configured to determine a posture rating of the wearer from the signal of the one or more posture sensors.

In certain embodiments, the biofeedback system further comprises a display for displaying the posture rating.

In order to provide active and passive corrective forces that address different spinal conditions, a double layer design including an inner layer and an outer layer is used for the bracewear, and a biofeedback system is provided for posture training.

In certain embodiments, the inner layer of the bracewear comprises a tightly fitted vest made of knitted fabrics to provide a perfect fit on wearers as well as stabilize their torso movement. An open-chest bolero design can be used for the upper front of the bracewear so that pressure is not induced on the users. Flexible materials can be used for the bracewear to reduce lower back pain and support the back while the core and paraspinal muscles are strengthened by actively training the user to maintain an optimum posture.

In order to improve sagittal balance, sufficient pulling force to the upper back and shoulders is required. Accordingly, the strap assembly coupled with the rigid connector not only open up the chest and shoulders, but also help to maintain good alignment at the shoulder level and prevent shoulder rotation. The strap assembly includes a left shoulder strap and right shoulder strap, which are joined at the rigid connector. Their tension can be adjusted to stabilize the position of the shoulders. Different patterns and materials can be used to enhance the level of comfort as well as maintain sufficient tension. Neoprene can be used as the material instead of foam because it offers better stretch and recovery properties.

The strap assembly can also control shoulder orientation. The left and right shoulder straps of the strap assembly are joined at the highest level of the hunchback and are further wrapped across the pelvis and fixed at the front of waistband. This design allows the separation of the strap assembly into left and right components. Therefore, the tension of the straps can be adjusted separately, which controls the open chest bolero and reduces rounded shoulders.

It has been observed that prolonged bracing in older patients can lead to the deconditioning of the paraspinal muscles and worsening of the deformity and symptoms. The effectiveness of bracing would be enhanced if both passive and active corrective effects are offered. Therefore, the biofeedback system provides a non-invasive treatment method that trains the wearers to reduce their physical ailments and improve health conditions by monitoring their physiological signals.

Figure 1A:
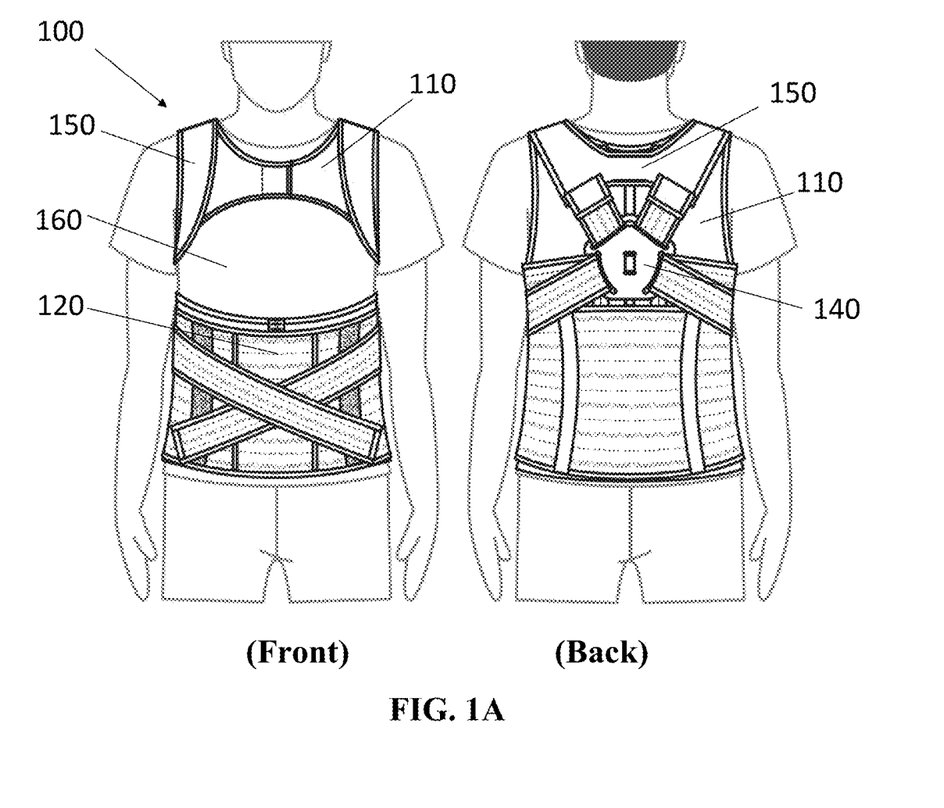
FIG. 1A depicts a bracewear for spinal correction according certain embodiments.

FIG. 1A depicts a bracewear 100 for spinal correction for a wearer 160 according certain embodiments. The bracewear 100 comprises a vest 110, a waistband 120, two back struts 130a, 130b (shown in FIG. 1D), a rigid connector 140 and a strap assembly 150. The vest 110 is wearable by the wearer 160. The waistband 120 surrounds the abdomen of the wearer 160 to provide support and a shaping effect. The two struts 130a, 130b are attached to the back of the vest 110 for supporting the spine of the wearer 160. The rigid connector 140 overlies the two back struts 130a, 130b to apply a force 145 (shown in FIG. 1H) to the two back struts 130a, 130b. The strap assembly 150 surrounds the shoulders and pelvis of the wearer 160 and connects to the rigid connector 140.

Figure 1B:
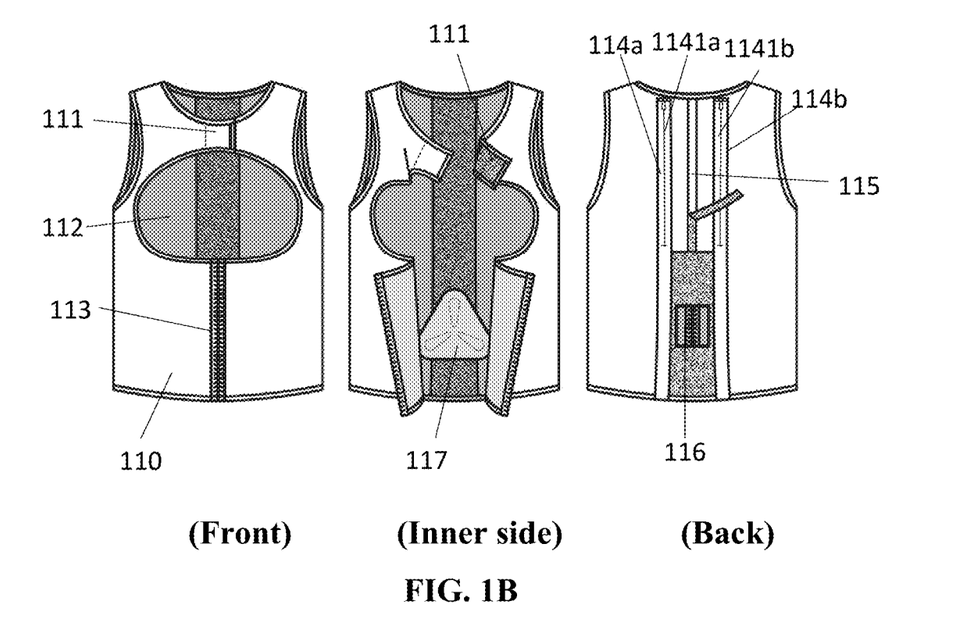
FIG. 1B depicts the vest of FIG. 1A.

As shown in FIG. 1B, the vest 110 comprises a separable collar 111, a front hole 112, a zipper 113, two strut casings 114a, 114b, a connector fixer 115, a back hole 116. The separable collar 111 is separable and adjustable in length for providing better fitting to the wearer 160, and a hook-and-loop fastener is used for fastening the separable collar 111. The front hole 112 is located on the upper front of the vest 100 below the separable collar 111 for avoiding inducing pressure on the upper front of the wearer 160. The zipper 113 is attached to the lower part of the vest 110 such that the vest 110 can be easily opened and closed for facilitating the wearing of the vest 110. The two strut casings 114a, 114b are attached to the back of the vest 100 adjacent to the vertical middle of the vest 100 for holding the two back struts 130a, 130b respectively. The strut casing 114a has a zipper 1141a for closing and opening the strut casing 114a. The strut casings 114b has a zipper 1141b for closing and opening the strut casing 114b. The connector fixer 115 is a strap attached to the back of the vest 110 along the vertical middle of the vest 100 by a hook-and-loop fastener and located between the two strut casings 114a, 114b for fixing the rigid collector 140 in position. The back hole 116 is located on the back of the vest for accommodating a controller. A lumbar pad 117 is attached to the back of the vest 100.

Figure 1C:
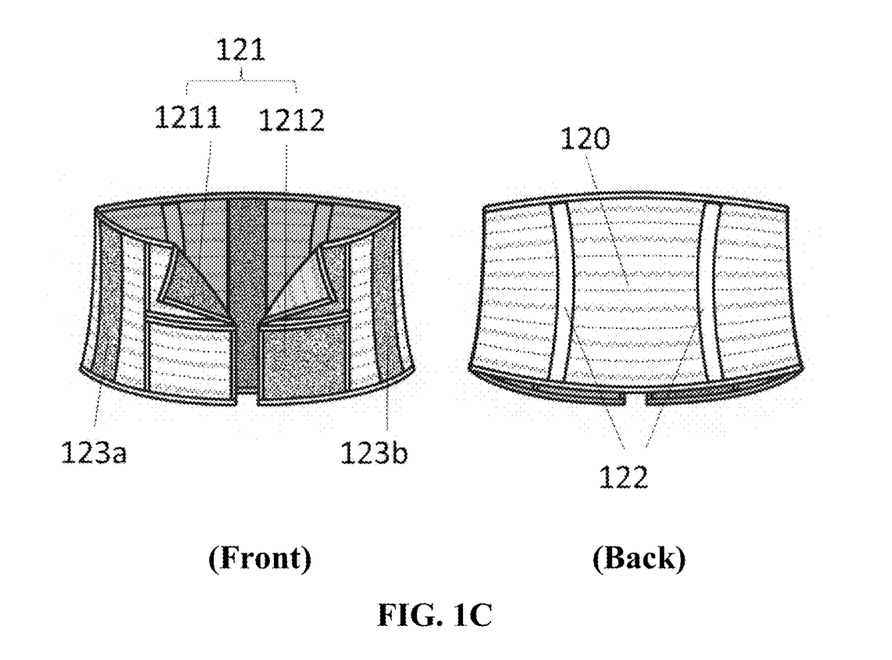
FIG. 1C depicts the waistband of FIG. 1A.

As shown in FIG. 1C, the waistband 120 is separable and adjustable in length and comprises a hook-and-loop fastener 121, a plurality of resin struts 122 and two lineal fabric straps 123a, 123b. The hook-and-loop fastener 121 fastens the waistband 112 in suitable length and comprises two lineal fabric straps 1211, 1212. The lineal fabric 1211 contains hooks and is attached to the back surface of the waistband 120. The lineal fabric 1212 contains loops and is attached to the front surface of the waistband 120. The resin struts 122 provide better support to the waistband 120. The two lineal fabric straps 123a, 123b contain loops for connecting the strap assembly 150 to the waistband 120.

Figure 1D:
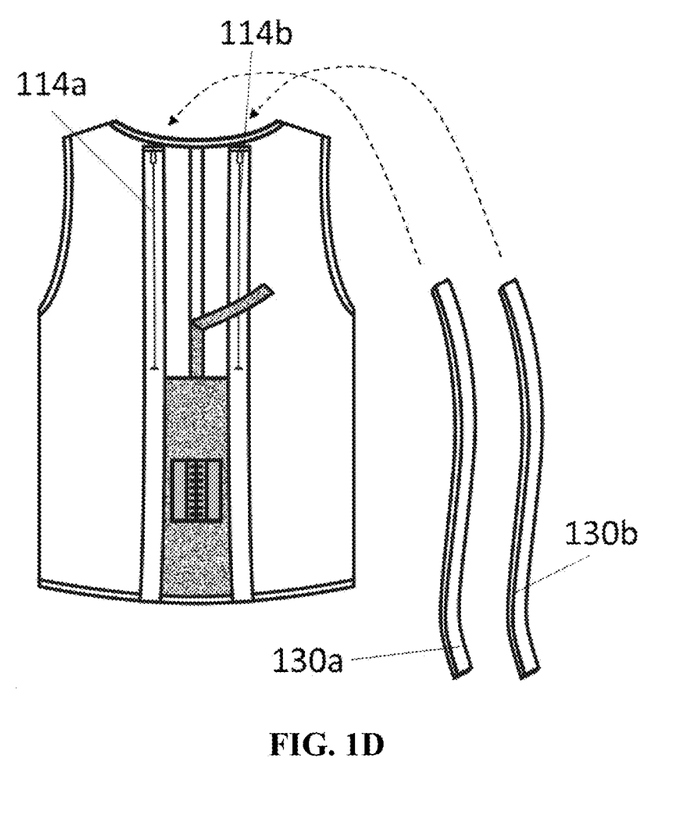
FIG. 1D depicts the back struts of the bracewear.

As shown in FIG. 1D, the back struts 130a, 130b have an elongated shape with a curvature for aligning the spinal curvature of the wearer 160, and can be accommodated in the strut casings 114a, 114b respectively.

Figure 1E:
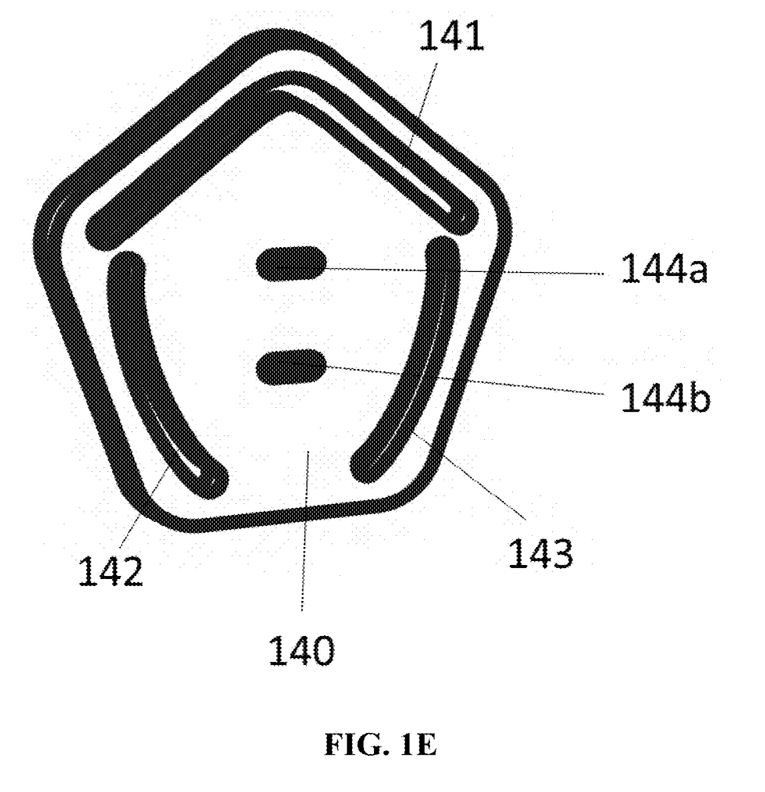
FIG. 1E depicts the rigid connector of FIG. 1A.

As shown in FIG. 1E, the rigid connector 140 is a pentagon-shaped plate comprising an upper slot 141, a left bottom slot 142, a right bottom slot 143 and two fixer slots 144a, 144b. The upper slot 141, the left bottom slot 142 and the right bottom slot 143 are used for connecting the rigid connector 140 to the strap assembly 150. The two fixing slots 144a, 144b located at the center of the plate allow the connector fixer 115 to pass through for fixing the rigid connector 140 in position.

Figure 1F:
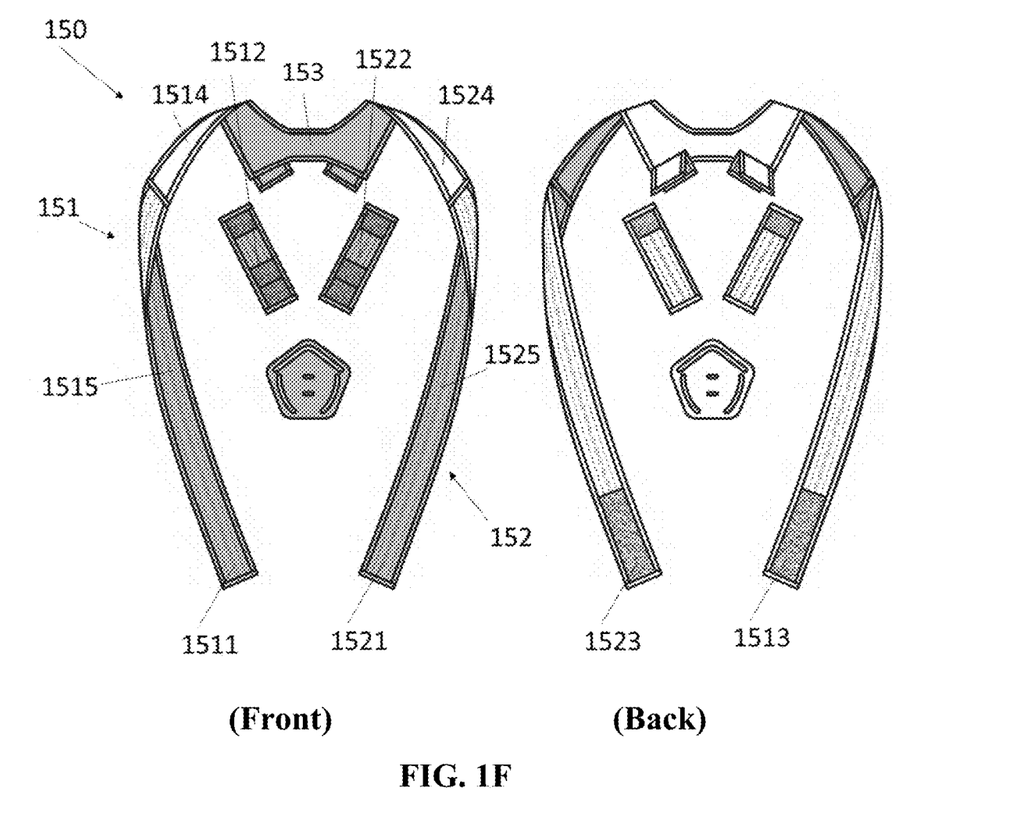
FIG. 1F depicts the strap assembly of FIG. 1A before assembling.
Figure 1G:
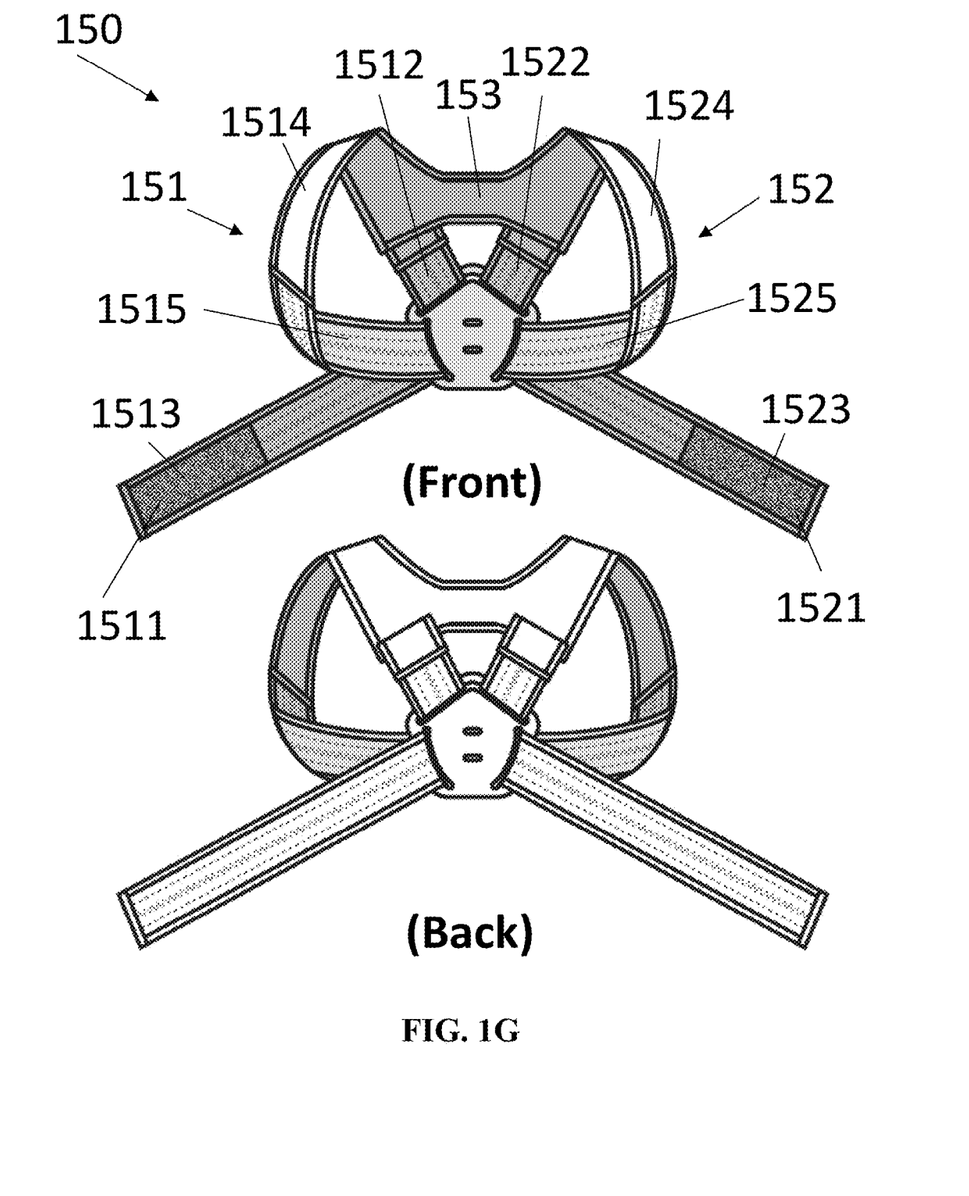
FIG. 1G depicts the strap assembly of FIG. 1A after assembling.

As shown in FIGS. 1F and 1G, the strap assembly 150 comprises a first shoulder strap 151, a second shoulder strap 152 and a strap connector 153. The strap connector 153 connects the first shoulder strap 151 and the second shoulder strap 152 together for forming the strap assembly 150 in a whole structure. The first shoulder strap 151 is used for surrounding the left shoulder and the left side of the pelvis of the wearer 160. The first shoulder strap 151 has a first end 1511 and a second end 1512. A lineal fabric strap 1513 having hooks is attached to the first end 1511 such that the first end 1511 is attachable to the waistband 120 by pressing the lineal fabric strap 1513 and the lineal fabric strap 123b together. The second shoulder strap 152 is used for surrounding the right shoulder and the right side of the pelvis of the wearer 160. The second shoulder strap 152 has a first end 1521 and a second end 1522. A lineal fabric strap 1523 having hooks is attached to the first end 1521 such that the first end 1521 is attachable to the waistband 120 by pressing the lineal fabric strap 1523 and the lineal fabric strap 123a together.

Figure 1H:
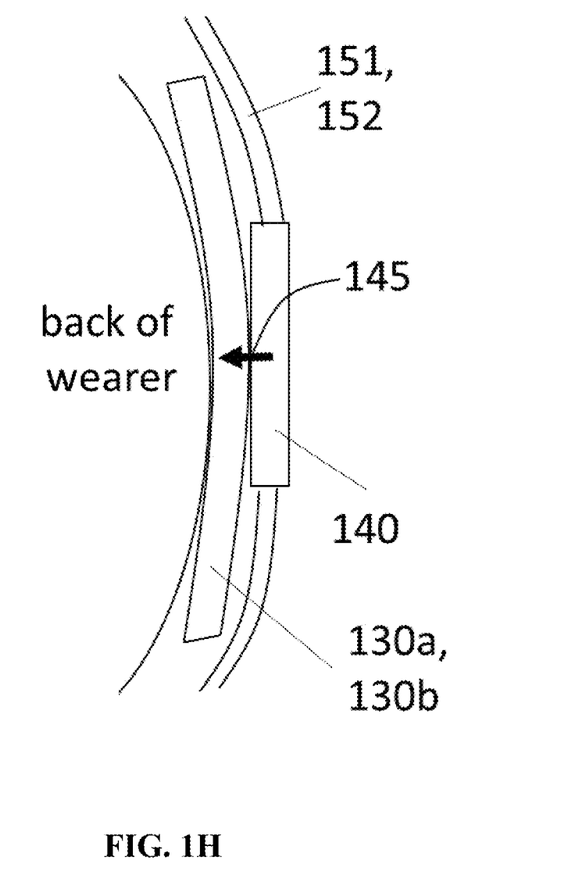
FIG. 1H depicts a force applied to the back struts of FIG. 1D.

The second end 1512 of the first shoulder strap 151 passes through the upper slot 141 and fastens in a loop by a hook-and-loop fastener to connect to the upper slot 141. The length of the second end 1512 is adjustable by fastening it with the loop with different dimensions. The first shoulder strap 151 passes through the left bottom slot 142 for surrounding the left shoulder and is wrapped around the left side of the pelvis, and then the first end 1511 is attached to the waistband 120. The second end 1522 of the second shoulder strap 152 passes through the upper slot 141 and fastens in a loop by a hook-and-loop fastener to connect to the upper slot 141. The length of the second end 1522 is adjustable by fastening it with the loop with different dimensions. The second shoulder strap 152 passes through the right bottom slot 143 for surrounding the right shoulder and is further wrapped around the right side of pelvis, and then the first end 1521 is attached to the waistband 120. Accordingly, the rigid connector 140 overlies the two back struts 130a, 130b. When the first shoulder strap 151 and the second shoulder strap 152 are under tension, the rigid connector 140 applies a force 145 to the back struts 130a, 130b to press the back of the wearer 160 so as to correct the alignment of the spine as shown in FIG. 1H.

In this embodiment, the first shoulder strap 151 comprises a non-elastic portion 1514 and an elastic portion 1515. The non-elastic portion 1514 is located between the second end 1512 and the elastic portion 1515 for surrounding the left shoulder with better support. The elastic portion 1515 is located between the first end 1511 and the non-elastic portion 1514 for facilitating the attachment of the first end 1511 to the waistband 120 by adjusting the length of the elastic portion 1515 as well as the adjustment of the force 145 in an appropriate amount. The second shoulder strap 152 comprises a non-elastic portion 1524 and an elastic portion 1525. The non-elastic portion 1524 is located between the second end 1522 and the elastic portion 1525 for surrounding the right shoulder with better support. The elastic portion 1525 is located between the first end 1521 and the non-elastic portion 1524 for facilitating the attachment of the first end 1521 to the waistband 120 by adjusting the length of the elastic portion 1525 as well as the adjustment of the force 145 in an appropriate amount.

Figure 1I:
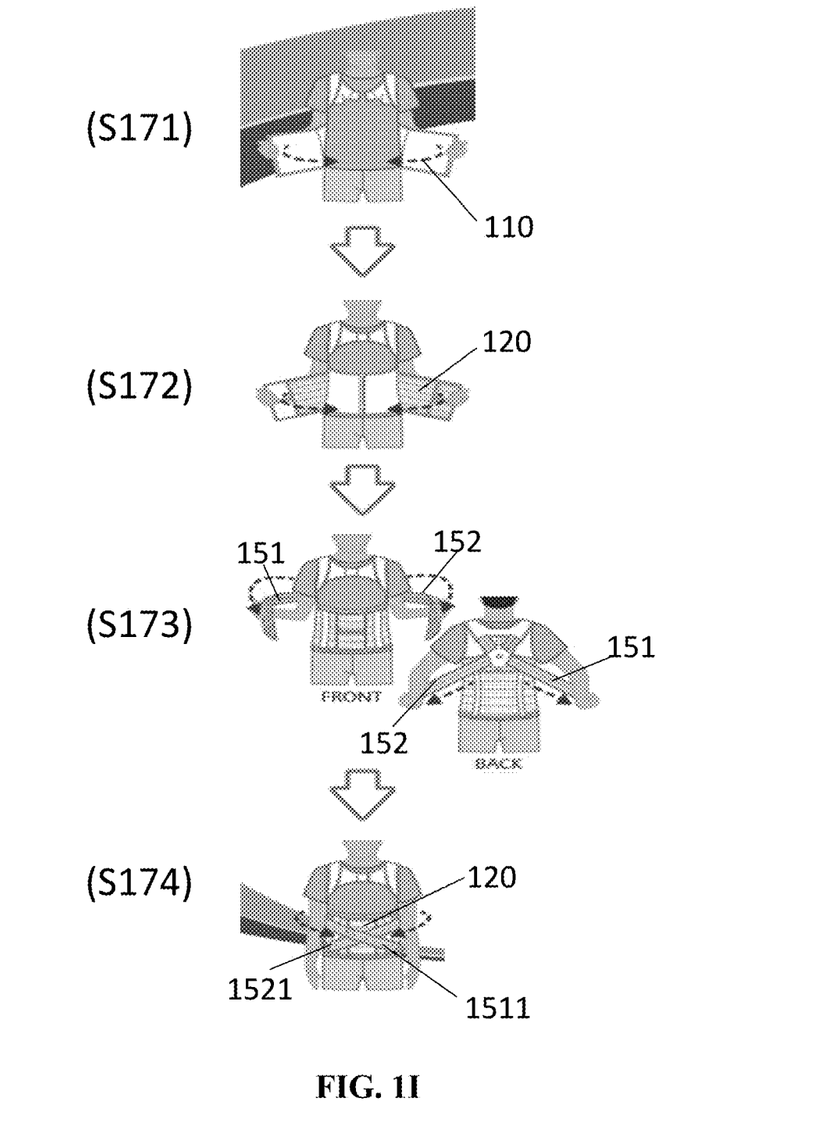
FIG. 1I depicts a process flow for wearing the bracewear of FIG. 1A.

FIG. 1I depicts a process flow for wearing the bracewear. In step S171, the wearer holds his body upright, lets his arms to go through the shoulders of the vest 110, connects the separable collar with the hook-and-loop fastener and zips the vest 110 up. In step S172, the wearer 160 fastens the waistband 120 firmly on his abdomen. In step S173, the wearer 160 lets his arms to go through the first shoulder strap 151 and the second shoulder strap 152 and pulls down the first shoulder strap 151 and the second shoulder strap 152 until his shoulders and back are restrained. In step S174, the wearer 160 tightens the first shoulder strap 151 and the second shoulder strap 152 to a comfortable level and attaches the first end 1511 and the first end 1521 to the bottom of the waistband 120 to fix the bracewear into place.

In certain embodiments, the vest and the strap assembly are made of flexible breathable textiles instead of non-breathable and rigid materials in order to enhance the wear comfort which can encourage treatment compliance.

In certain embodiments, the 3D printed back struts are used to support the spine and modify the curvature of the spine. They can be customized based on the spinal curvature as well as the progression of the treatment. Carbon reinforced nylon can be used for the back struts owing to light in weight and high strength and modulus.

In certain embodiments, the rigid connector is a metal buckle or a plastic buckle.

In certain embodiments, the rigid connector is placed above the highest level of the hump of the back curvature in order to adjust the location and tension of the straps. Therefore, the optimum corrective force can be exerted onto the upper back.

In certain embodiments, magnetic zippers and hook-and-loop fasteners are used for assembling the bracewear to increase the ease of assembling and donning of the bracewear. The hook-and-loop fasteners can be attached to the bracewear by sewing or adhesion.

In certain embodiments, lumbar pads can be attached to anywhere of the vest based on the spinal conditions of a wearer for spinal correction. The lumbar pad can comprise silicon.

Figure 2:
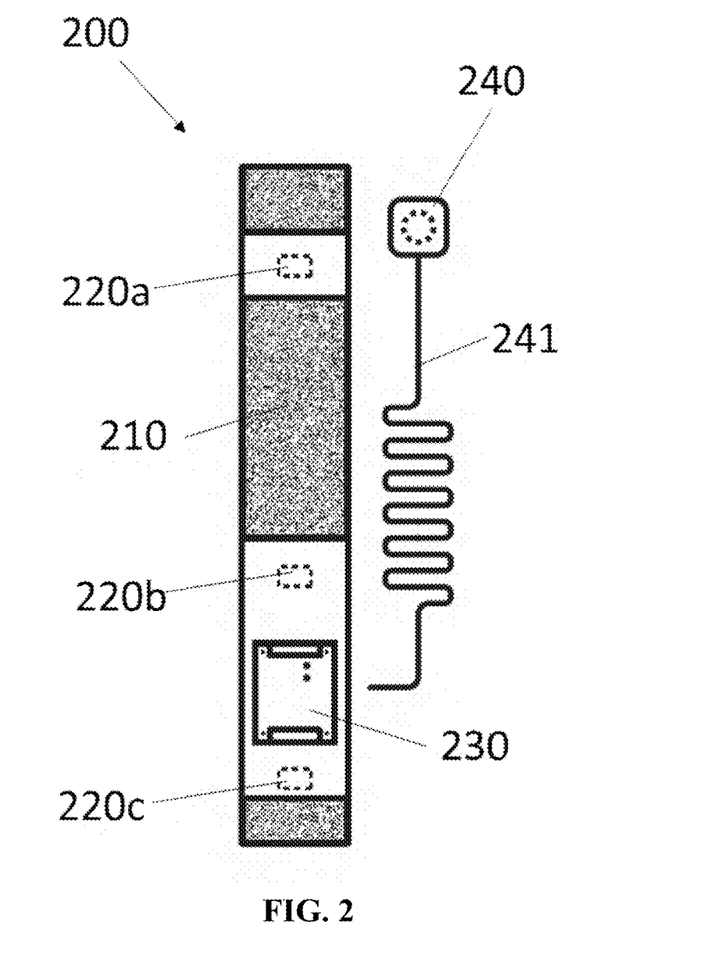
FIG. 2 depicts a biofeedback system for posture training according to certain embodiments.

FIG. 2 depicts a biofeedback system 200 for posture training according to certain embodiments. The biofeedback system 200 comprises a sensor strap 210, three posture monitoring sensors 220a, 220b, 220c, a controller 230 and a vibrator 240. The three posture monitoring sensors 220a, 220b, 220c monitor the posture of a wearer, are attached to the sensor strap 210 and connected to the controller 240 by cables. The controller 230 is attached to the sensor strap 210 and connected to the vibrator via a cable 241. The controller 230 determines the posture of the wearer from the signals of the three posture monitoring sensors 220a, 220b, 220c and control the vibrator 240 to vibrate for alerting the wearer when the wearer is in bad posture.

In certain embodiments, three posture monitoring sensors are placed along the spinal column which are above and below the apex of the thoracic kyphosis and lumbar lordosis respectively, such that the upper and lower trunk movements can be detected and the misalignment of the body can be identified immediately.

In certain embodiments, the posture monitoring sensor is an inertial measurement unit for identifying six axis movements to manage posture deviations.

Figure 3A:
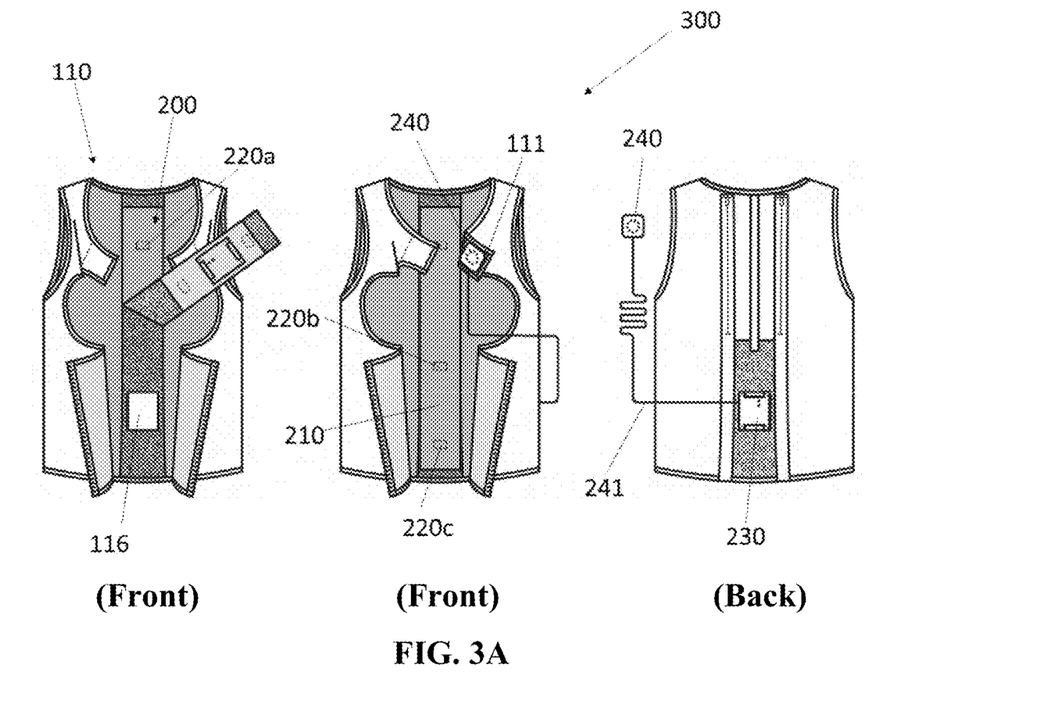
FIG. 3A depicts a system for posture training according to certain embodiments.
Figure 3B:
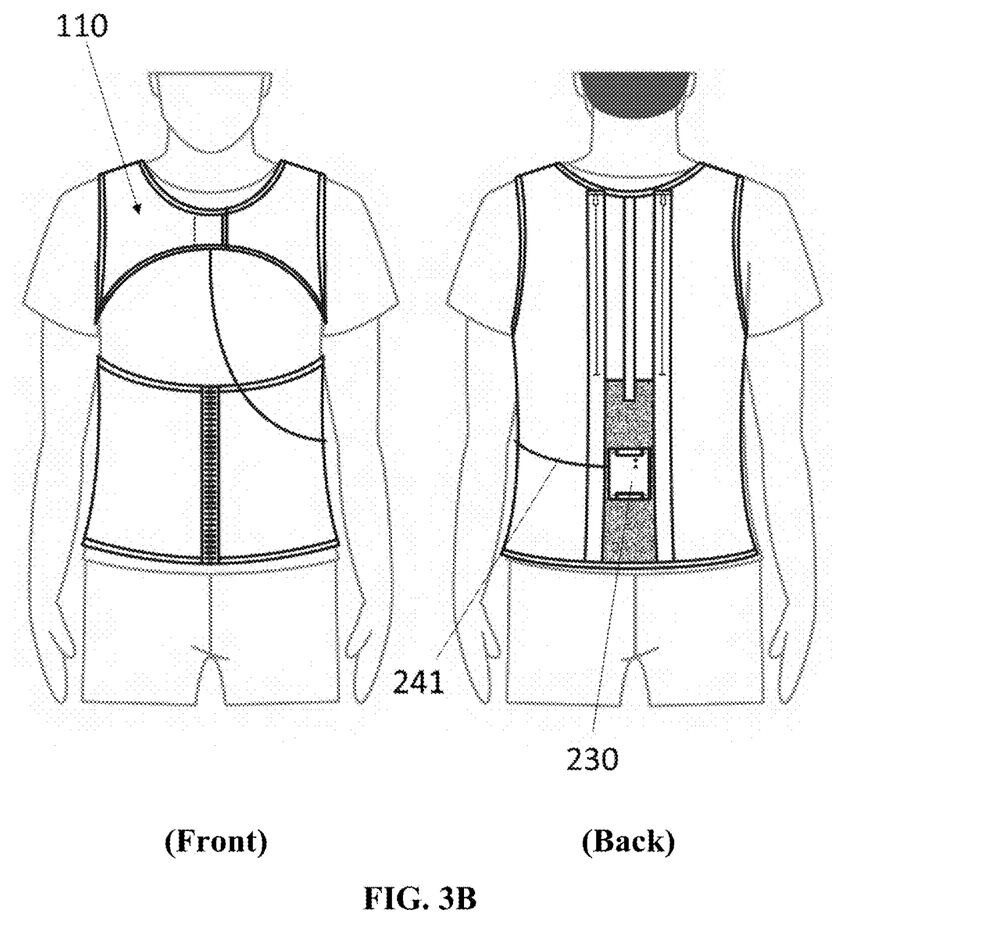
FIG. 3B depicts the system of FIG. 3A worn by a wearer.

FIGS. 3A and 3B depicts a system 300 for posture training for a wearer according to certain embodiments. The system 300 comprises the biofeedback system 200 of FIG. 2 and the vest 110 of FIG. 1A. The sensor strap 210 is attached to the back of the vest 110 along the vertical middle by a hook-and-loop fastener such that the three posture monitoring sensors 220a, 220b, 220c are located along the top, middle and bottom of the spine of the wearer respectively. The controller 230 is located at the back hole 116. The vibrator 240 is attached to the separable collar 111 and connected to the controller 230 via the cable 241.

In certain embodiments, the vest comprises a plurality of protective cases for accommodating the sensors, the vibrator, the controller and the cables.

Figure 3C:
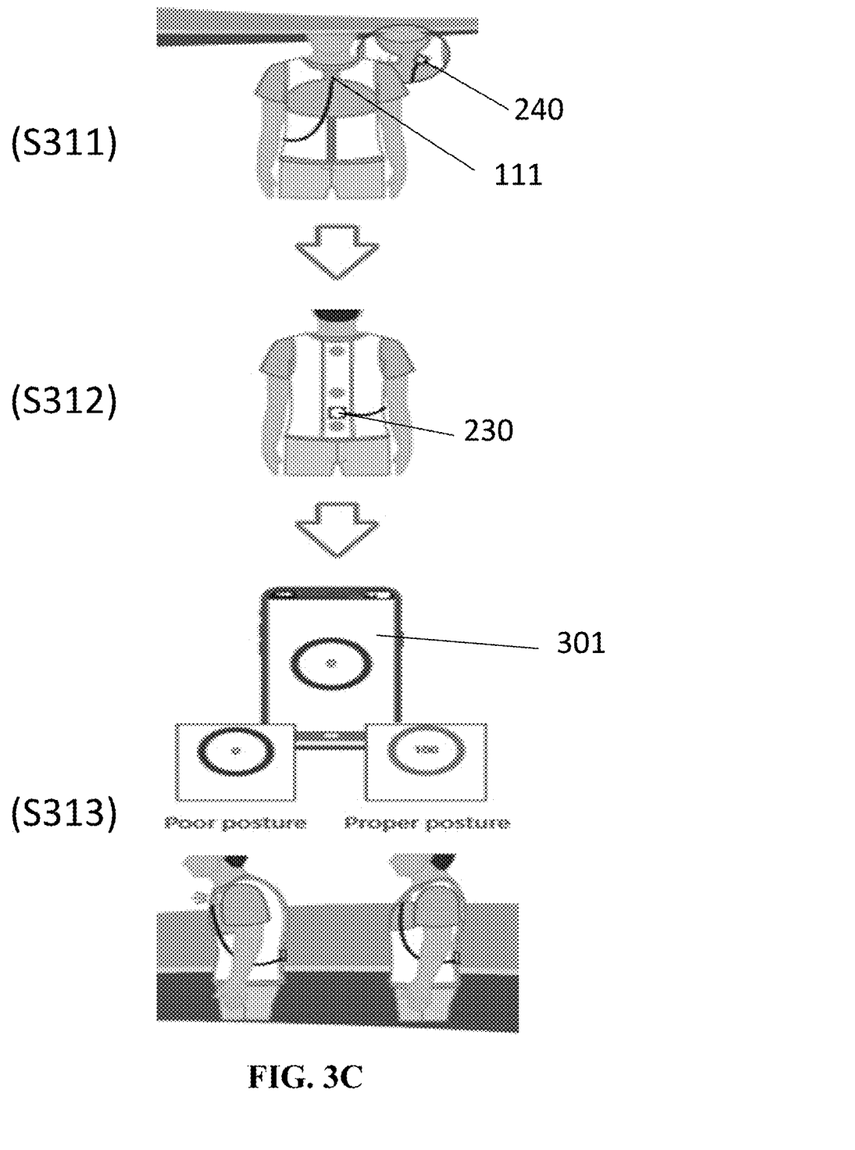
FIG. 3C depicts a process flow for posture training according to certain embodiments.

FIG. 3C depicts a process flow for posture training for a wearer according to certain embodiments. In step S311, the vibrator 240 is attached to the separable collar 111. In step S312, the mobile application of a mobile device 301 is switched on and the mobile device 301 is connected to the controller 230 via Bluetooth. In step S313, once the controller 230 has detected a bad posture, real-time feedback is provided by the vibration of the vibrator 240 at the separable collar 111 until that the posture is corrected. The wearer can review the posture rating on the mobile device 301 in a range from 0 mark (extremely poor performance) to 100 marks (extremely poor performance).

According to certain embodiments, the present system is applicable to the people, who are diagnosed with degenerative scoliosis and lower back pain, or the elderly.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A bracewear for spinal correction for a wearer comprising:
   a vest wearable by the wearer;
   a waistband for surrounding an abdomen of the wearer;
   one or more back struts arranged to be attached to a back of the vest for supporting a spine of the wearer;
   a rigid connector arranged to overlie the one or more back struts o applying a force to the one or more hack struts; and
   a strap assembly comprising:
      a first shoulder strap for surrounding a left shoulder of the wearer and a left side of a pelvis of the wearer, a first end of the first shoulder strap being attachable to the waistband; and
      a second shoulder strap for surrounding a right shoulder of the wearer and a right side of the pelvis, a first end of the second shoulder strap being attachable to the waistband;
   wherein the first shoulder strap, the second shoulder strap and the rigid connector are configured to connect the first shoulder strap and the second shoulder strap to the rigid connector such that when the first shoulder strap and the second shoulder strap are under tension, the rigid connector applies the force to the one or more back struts so as to correct alignment of the spine,
   wherein the first shoulder strap comprises a first non-elastic portion and a first elastic portion, the first non-elastic portion being used for surrounding the left shoulder, the first elastic portion being used for connecting to the rigid connector and surrounding the left side of the pelvis; and the second shoulder strap comprises a second non-elastic portion and a second elastic portion, the second non-elastic portion being used for surrounding the right shoulder, the second elastic portion being used for connecting to the rigid connector and surrounding the right side of the pelvis.

2. The bracewear of claim 1, wherein the rigid connector comprises:
   a first slot for connecting to a second end of the first shoulder strap and a second end of the second shoulder strap;
   a second slot for allowing the first shoulder strap to pass through; and
   a third slot for allowing the second shoulder strap to pass through.

3. The bracewear of claim 1, wherein the rigid connector comprises:
   a first slot fir connecting to a second end of the first shoulder strap;
   a second slot for connecting to a second end of the second shoulder strap;
   a third slot for allowing the first shoulder strap to pass through; and
   a fourth slot for allowing the second shoulder strap to pass through.

4. The bracewear of claim 1, wherein each of the first non-elastic portion and the second non-elastic portion comprises a laminated neoprene fabric; and each of the first elastic portion and the second elastic portion comprises a knitted fabric.

5. The bracewear of claim 1, wherein each of the one or more back struts has a curvature fitting the spine.

6. The bracewear of claim 1, wherein the vest comprises one or more strut casings attached to the back of the vest for holding the one or more hack struts respectively.

7. The bracewear of claim 1, wherein the vest comprises a connector fixer attached to the back of the vest for fixing the rigid connector to overlie the one or more back struts.

8. The bracewear of claim 7, wherein the rigid connector comprises one or more slots, and the connector fixer comprises a strap for passing through the one or more slots.

9. The bracewear of claim 1, wherein the vest has a separable collar and comprises a front hole located below the separable collar.

10. The bracewear of claim 1 further comprising:
one or more posture monitoring sensors attachable to the back of the vest for monitoring a posture of the wearer;
an alerting device for alerting the wearer when the wearer is in poor posture; and
a controller configured to:
determine the posture from a signal from the one or more posture sensors; and
control the alerting device for alerting the wearer when the wearer is in poor posture.

11. A system for posture training for a wearer comprising:
the bracewear of claim 1; and
a biofeedback system comprising:
one or more posture monitoring sensors attachable to the back of the vest for monitoring a posture of the wearer;
an alerting device for alerting the wearer when the wearer is in bad posture; and
a controller configured to:
determine the posture from a signal of the one or more posture sensors; and
control the biofeedback system to alert the wearer when the wearer is in bad posture.

12. The system of claim 11, wherein each of the one or more posture monitoring sensors is an inertial measurement unit for measuring orientation of the spine of the wearer.

13. The system of claim 11, wherein the alerting device is a vibrator or a buzzer.

14. The system of claim 11, wherein the controller is further configured to determine a posture rating of the wearer from the signal of the one or more posture sensors.

15. The system of claim 14, wherein the biofeedback system further comprises a display for displaying the posture rating.

16. The system of claim 11, wherein the one or more posture monitoring sensors are attached to the back of the vest; and the alerting device is attached to a collar of the vest.

* * * * *